United States Patent [19]
Johnson

[11] Patent Number: 5,972,027
[45] Date of Patent: Oct. 26, 1999

[54] POROUS STENT DRUG DELIVERY SYSTEM

[75] Inventor: Michael W. Johnson, Plymouth, Minn.

[73] Assignee: Scimed Life Systems, Inc, Maple Grove, Minn.

[21] Appl. No.: 08/940,696

[22] Filed: Sep. 30, 1997

[51] Int. Cl.$^6$ ............................................. A61F 2/06
[52] U.S. Cl. ........................ 623/1; 623/12; 424/422; 424/423
[58] Field of Search .................... 623/1, 11, 12, 623/16; 606/108, 191, 194, 195, 198; 424/422, 423

[56] References Cited

U.S. PATENT DOCUMENTS

| | | | |
|---|---|---|---|
| 4,073,999 | 2/1978 | Bryan et al. | 428/311 |
| 4,082,893 | 4/1978 | Okita | 428/376 |
| 4,101,984 | 7/1978 | MacGregor | 3/1.5 |
| 4,208,745 | 6/1980 | Okita | 623/1 |
| 4,222,977 | 9/1980 | Dobo | 264/63 |
| 4,405,319 | 9/1983 | Cosentino | 604/175 |
| 4,770,664 | 9/1988 | Gogolewski | 623/66 |
| 4,784,159 | 11/1988 | Szilagyi | 128/784 |
| 4,784,160 | 11/1988 | Szilagyi | 128/784 |
| 4,850,999 | 7/1989 | Planck | 623/1 |
| 5,019,090 | 5/1991 | Pinchuk | 606/194 |
| 5,059,166 | 10/1991 | Fischecll et al. | 600/3 |
| 5,104,403 | 4/1992 | Brotuzu et al. | 623/1 |
| 5,116,360 | 5/1992 | Pinchuk et al. | 623/1 |
| 5,132,080 | 7/1992 | Pfeil | 419/2 |
| 5,163,958 | 11/1992 | Pinchuk | 623/11 |
| 5,176,617 | 1/1993 | Fishell et al. | 600/3 |
| 5,222,971 | 6/1993 | Willard et al. | 606/158 |
| 5,226,913 | 7/1993 | Pinchuk | 623/1 |
| 5,234,458 | 8/1993 | Metais | 606/200 |
| 5,342,348 | 8/1994 | Kaplan | 604/891.1 |
| 5,383,928 | 1/1995 | Scott et al. | 623/1 |
| 5,449,382 | 9/1995 | Dayton | 623/1 |
| 5,618,298 | 4/1997 | Simon | 606/194 |
| 5,641,443 | 6/1997 | Calcote et al. | 264/127 |
| 5,707,385 | 1/1998 | Williams | 606/192 |
| 5,749,880 | 5/1998 | Banas et al. | 606/198 |
| 5,769,884 | 6/1998 | Solavay | 623/12 |
| 5,772,748 | 6/1998 | Hubbard | 106/38.27 |
| 5,817,126 | 10/1998 | Imran | 623/12 |
| 5,843,172 | 12/1998 | Yan | 623/1 |
| 5,855,600 | 1/1999 | Alt | 623/12 |
| 5,882,335 | 3/1999 | Leone et al. | 604/96 |

FOREIGN PATENT DOCUMENTS

| | | | |
|---|---|---|---|
| 90/13332 | 11/1990 | WIPO | A61M 31/00 |
| WO 91/17789 | 11/1991 | WIPO | A61M 29/02 |
| 96/01733 | 1/1996 | WIPO | B32B 3/10 |
| WO 96/00103 | 1/1996 | WIPO | A61M 29/00 |
| 96/32907 | 10/1996 | WIPO . | |
| 98/32412 | 7/1998 | WIPO . | |

OTHER PUBLICATIONS

J. Kroschwitz, ed., Concise Encyclopedia of Polymer Science and Engineering, p. 1167, 1990.
K.H. Roll, Kirk–Othmer Concise Dictionary of Chemical Technology, pp. 945–947, 1985.
FILTERMET product literature. Date unknown.

*Primary Examiner*—Mickey Yu
*Assistant Examiner*—Tram A. Nguyen
*Attorney, Agent, or Firm*—Vidas, Arrett & Steinkraus

[57] ABSTRACT

Expandable intraluminal stents made of a powdered metal or polymer are provided as well their method of manufacture. These stents are characterized by a desired porosity, with a drug compressed into the pores of the stent. The stents are formed by subjecting one or more powdered materials in a die cavity to a pressure treatment followed by a heat treatment. The material may be cast directly in a stent-like form or cast into sheets or tubes from which the inventive stents are produced. The so-formed porous metal or polymer stent is then loaded with one or more drugs.

9 Claims, 3 Drawing Sheets

POROUS STENT DRUG DELIVERY SYSTEM

BACKGROUND OF THE INVENTION

This invention relates to stents for maintaining the patency of body passages. Additionally, the stents may serve as drug delivery vehicles. The invention has particular application to stenting in blood vessels of the human body and will be described with reference thereto. However, in a broader sense it relates to stenting in any body passage, including such passages as the gastrointestinal tract, urethral and ureteral tracts, bronchial and esophageal tracts. The invention also has particular reference to stents comprising compounds useful for the treatment and prevention of restenosis and also will find application in dilating and maintaining the patency of various body passages such as ureters and the like.

SUMMARY OF THE INVENTION

In accordance with the present invention, a porous stent made from a powdered metal or polymeric material is disclosed. The inventive stent is an expandable intraluminal stent comprising a main body portion having a first end, a second end and a flow passage defined therethrough, the main body portion being sized for intraluminal placement within a body passage and subsequent expansion for implantation. The main body portion of the stent of the present invention is further characterized in that it is formed at least in part of at least one porous material, the porous material having been formed from a powdered metal or polymeric material.

In another embodiment of the present invention, a drug is contained within the pores of the stent for delivery to the body.

In another embodiment of the present invention, the stent may be coated with a drug.

In another embodiment of the present invention, the stent is comprised of at least two porous metals.

The present invention is also directed to a method for making a porous expandable intraluminal stent comprising the steps of providing a powdered material, subjecting the powdered material to high pressure to form a compact, sintering the compact to form a final porous material and forming a stent from the porous material. In another embodiment of the above-mentioned inventive method, at least one drug is loaded into the pores of the stent.

DETAILED DESCRIPTION OF THE PRESENTLY PREFERRED EXEMPLARY EMBODIMENTS

Figure 1A:
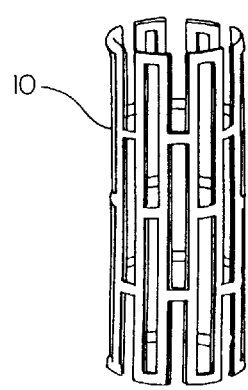
FIG. 1a is a perspective view of one embodiment of a stent according to the present invention.

The present invention relates to a porous stent made from a powdered material such as powdered metal or polymer for maintaining the patency of body passages. Stents to which the present invention relates may be either balloon expandable or self-expanding as well as springy in form. For example, self-expanding stents are known which are braided, woven or mesh-like in structure, although many other types of self-expanding stents including solid stents are also known. Such stents have memory characteristics and, if distorted in length and/or diameter by external forces, they will return or tend to return to a preformed configuration upon the release of external forces. This expansion may be due to the natural springiness of the stent, for instance with a rolled up sheet stent, or as a result of a phase transition occurring in the stent material. Balloon expandable stents may be expanded by the application of a suitable amount of force to the stent.

The stents of the present invention may be used to deliver drugs to a desired bodily location. As used in this application, the term "drug" denotes any compound which has a desired pharmacologic effect, or which is used for diagnostic purposes. Useful drugs, in the context of the present invention include, but are not limited to angiogenic drugs, smooth muscle cell inhibitors, collagen inhibitors, vasodilators, anti-platelet substances, anti-thrombotic substances, anti-coagulants, cholesterol reducing agents and combinations thereof. The drugs may include radiochemicals to irradiate and/or prohibit tissue growth or to permit diagnostic imaging of a site.

The porous stent may be used as a drug-delivery system to, for example, prevent restenosis. The drugs may include radiochemicals to irradiate and prohibit tissue growth. Angioplasty and stent deployment may cause injury of the endothelial cell layer of blood vessels, causing smooth muscle cell proliferation, leading to restenosis. To control smooth muscle cell growth endothelialization of cells on the inner wall surface of vessels will prevent or prohibit the smooth muscle growth. To promote endothelialization human growth factors may be included in the outer layer and delivered.

The stent of the present invention may be formed of any bio-compatible powdered metals such as stainless steel. Powdered metals typically are available in powder sizes as small as 40 microns or less. While powdered metals of any powder size may be used in forming the stents of the present invention, preferably powders 40 microns or less will be used in forming the porous metal stent of the present invention. More preferably, powdered metals ranging in size from 6 to 12 microns will be used. Especially desirable are powders with good flow properties so that the particles may be dispensed easily into a die cavity for metal processing. Other suitable metals include, but are not limited to, spring steel, nitinol and titanium as well as any other bio-compatible metal which may become available in powdered form in the future. Suitable metals do not produce toxic reactions or act as carcinogens. The stent of the present invention may also be formed of bio-compatible powdered polymeric materials such as PTFE.

The stents of the present invention may also be prepared with different mean pore sizes. Pore size is an important parameter in that certain macromolecular drugs may be excluded from use where the pore size is very small. The pore size may also play a role in determining the extent of cellular infiltration or tissue ingrowth during implantation of the stent. While cellular ingrowth is sometimes desirable, it can also lead to complications such as infection and difficulty in removing the stent. Stents with a mean pore size of greater than about 10 microns can allow infiltration of cellular sized biomaterials; stents with mean pore sizes in the range of 1–10 microns may accommodate infiltration of some of the above bio-materials. Stents with pore sizes less than about 1 micron will not generally accommodate infiltration of any of the above biomaterials but can accommodate infiltration of macromolecular and small biomaterials. Thus, the pore size of the stent may be varied to foster or inhibit cellular infiltration and/or tissue ingrowth. Of course, the pore size may also be varied to facilitate delivery of drugs of different molecular sizes.

The material processing proceeds with a pressure treatment step in which the powdered material in a die cavity is subjected to pressures of up to twenty tons or more. At such high pressures, the powder begins to interlock, forming a compact with pockets of air remaining in the metal. The pressure treatment step usually proceeds at room temperature although warm or hot pressing may be used. Other techniques to form the compact, as known in the art, may be substituted for the pressure treatment step. The die cavity used in this step may be a stent die cavity to allow for direct casting of the stent or alternatively, may be for some other form such as a tube or a sheet. Following the pressure treatment step, the compact has sufficient strength to allow for routine handling without breakage.

After ejection from the die, the compact is sintered to form a coherent metal or polymer mass in the shape of the die. Alternatively, the pressure treatment step can be eliminated and the processing limited to a sintering in which the metal or polymer powder is heated in a die resulting in a low density, highly porous compound. Although the sintering step may actually partially melt the metal or polymer as in liquid-phase sintering, in the preferred embodiment, the sintering step does not melt the metal or polymer as the temperature is maintained below the melting point of elemental metal or any alloys that have formed or the polymer melting point. The sintered metal or polymer will exhibit a porosity ranging from less than 10 percent to about 80 percent of the total volume. The percentage porosity is a measure of the void space within the metal.

Figure 1B:
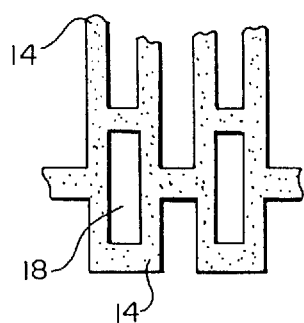
FIG. 1b is an enlargement of a portion of FIG. 1a showing pores on the surface of the metal.
Figure 2:
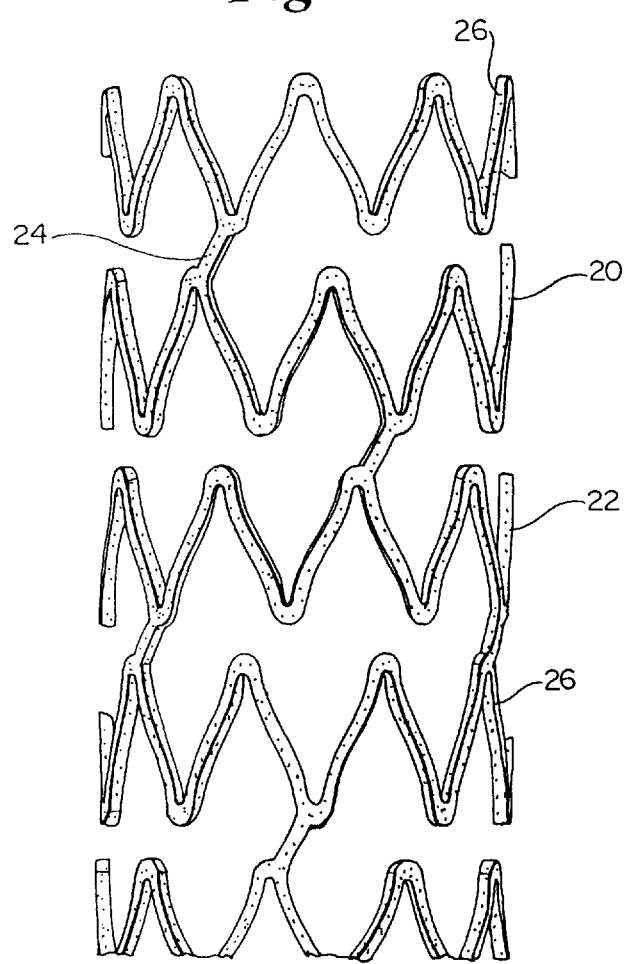
FIG. 2 is a sectional view of another embodiment of a stent in accordance with this invention.

Following sintering, the now porous metal or polymer may be formed into a stent, if it has not been so-formed already. Any known process in the art may be used including laser cutting and braiding of porous metal strands. FIGS. 1a and 1b illustrate one such stent 10, with pores 14 formed by laser cutting apertures 18 in a sheet of porous metal. FIG. 2 illustrates a stent 20 which is composed of a number of interconnected members 22, the members and interconnections 24 made of a metal containing pores 26. A braided stent may be formed of a series of strands arranged in a crossing configuration which may be woven, braided or the like. The strands of porous metal or polymer can be deformed so to provide a reduced diameter of the stent which facilitates its delivery to the targeted portion of a vessel or other passageway and once disposed at the target portion the stent can then be allowed to expand to its preformed configuration and larger diameter.

The stents of the present invention may be prepared in a range of porosities allowing for the production of stents with differing drug delivery characteristics. The porosity may be between twenty and eighty percent of the total volume and more suitably between forty and sixty percent of the volume.

The stent may be impregnated with one or more drugs by any known process in the art including high pressure loading in which the stent is placed in a bath of the desired drug or drugs and subjected to high pressure or, alternatively, subjected to a vacuum. The drug may be carried in a volatile or non-volatile solution. In the case of a volatile solution, following loading of the drug, the volatile carrier solution may be volatilized. In the case of the vacuum, the air in the pores of the metal stent is evacuated and replaced by the drug-containing solution.

In accordance with the present invention, the stent may further be coated with one or more layers of one or more drugs to allow for longer term drug elution optionally employing a number of different drugs over time. As such, the drug in the pores would not be eluted until the coating of drug has been absorbed, thereby allowing for longer term drug treatment than would be available from the coated metal alone.

Figure 3:
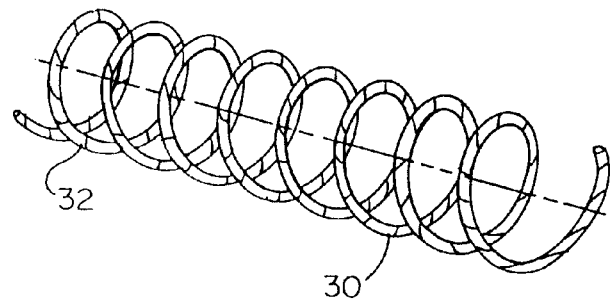
FIG. 3 is a perspective view of another embodiment of a stent according to the present invention.

FIG. 3 shows a coil stent 30 in which the porous metal stent 30 further comprises such a coating 32 (the pores have been omitted for clarity).

Figure 4A:
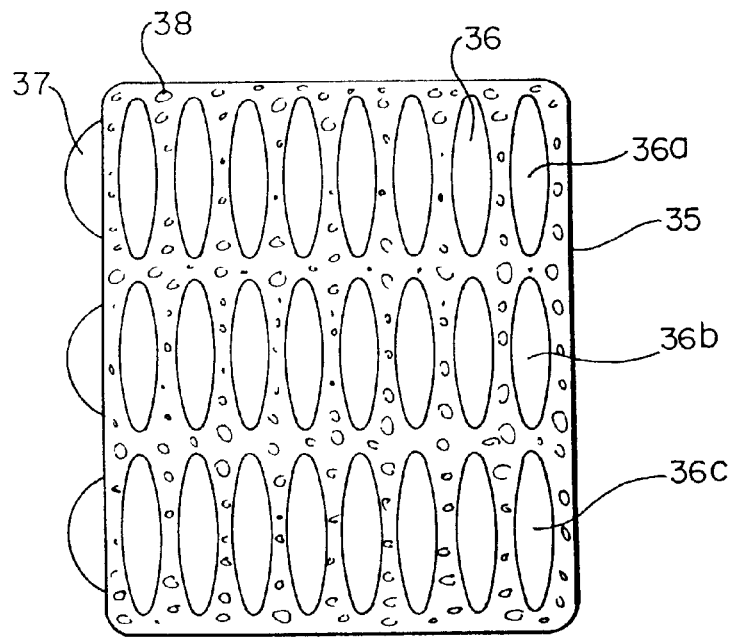
FIG. 4a is a plan view development of the inventive stent in sheet form prior to rolling.
Figure 4B:
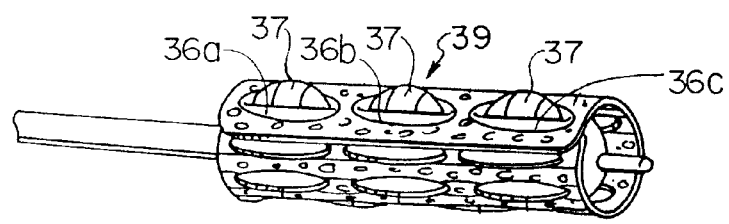
FIG. 4b is a sectional view of another embodiment of a stent according to the present invention.

The inventive stent may also be formed from a rolled up flat sheet comprised of a porous metal or polymer as shown in FIG. 4a. The sheet 35 contains a plurality of apertures 36 and pores 38 as well as tabs 37. The tabs are inserted into the holes 36a–c when the stent is rolled, as shown generally at 39 in FIG. 4b. The stent may be rolled tightly for delivery and implantation and be self-expandable to the extent that it tends to unroll. The stent may further be laminated with a layer of drug over the porous surface of the stent. Otherwise, it may simply be expanded by independent expansion means such as a balloon catheter positioned inside the stent as is already known in the art.

Another embodiment of the invention contemplates the fabrication of any stent design per se taken from the prior art, the stent prepared from a porous metal or polymer, the pores of the metal or polymer including one or more drugs.

Figure 5:
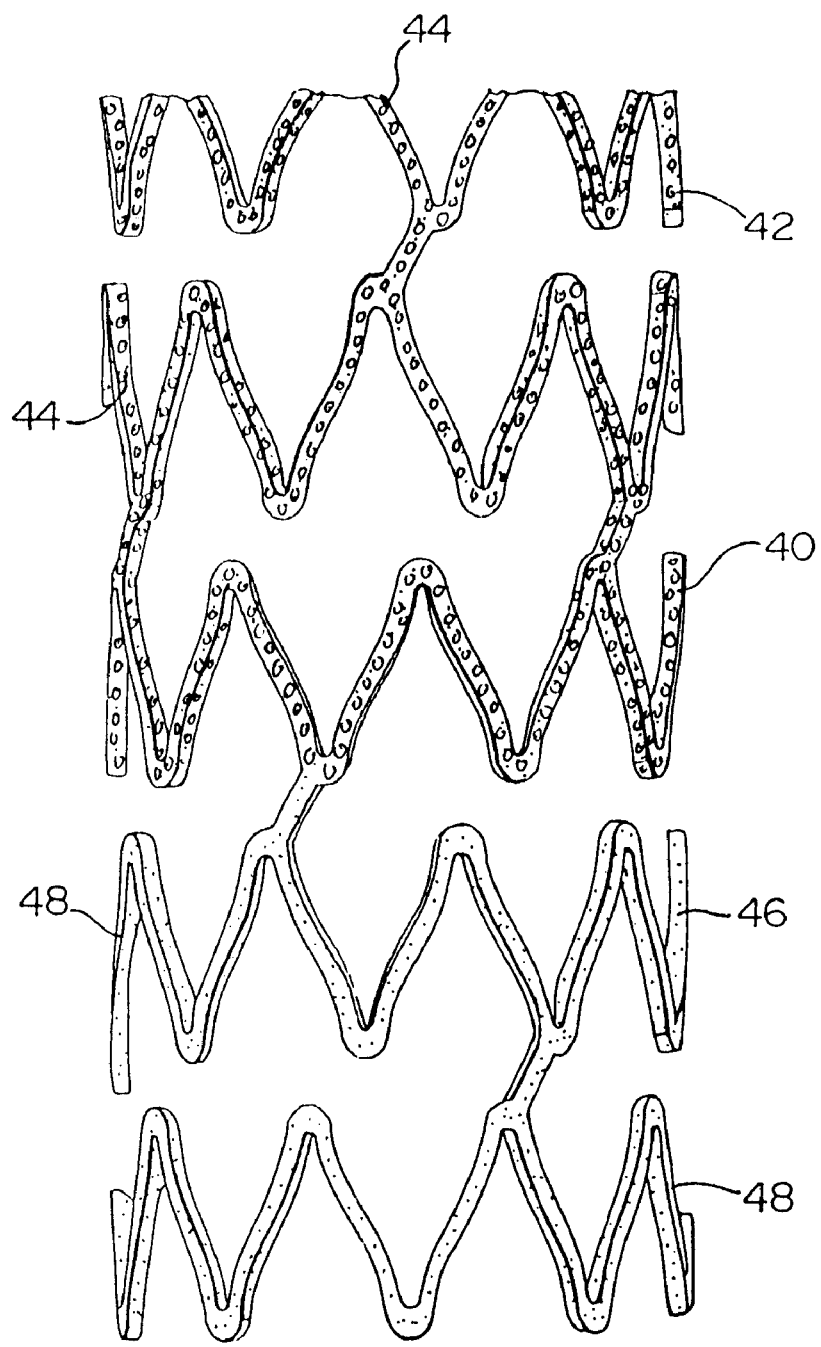
FIG. 5 is a perspective view of yet another embodiment of a stent according to this invention.

Another embodiment of the invention is an expandable intraluminal stent comprising a main body portion having a first end, a second end and a flow passage defined therethrough, the main body portion being sized for intraluminal placement within a body passage and subsequent expansion for implantation, the main body portion being further characterized in that it is formed at least in part of at least two metals, the two metals comprising a first porous metal characterized by a first porosity and mean pore size and a second porous metal characterized by a second porosity and mean pore size. FIG. 5 depicts one such stent, 40, the first metal 42 containing first pores 44 therein and the second metal 46 containing second pores 48 therein.

In the above embodiment, one drug may be loaded into the pores of the first porous metal and a second drug loaded into the pores of the second porous metal. Alternatively, the same drug can be loaded into both the first and second porous metals.

The present invention is also directed to a method for making a porous metal, expandable intraluminal stent comprising the steps of providing a powdered metal or polymeric material, subjecting the powder to high pressure to form a compact, sintering the compact to form a final porous metal or polymer, forming a stent from the porous metal and, optionally, loading at least one drug into the pores. The drug(s) may be loaded into the pores by placing the stent in a liquid bath comprising the at least one drug at high pressure, by placing the stent in a liquid bath within a chamber, the liquid bath comprising the drug(s), and reducing the pressure within the chamber below ambient pressure or by any other method known in the art.

In yet another embodiment, the invention is directed to a method of making an expandable intraluminal stent of varying porosity comprising the steps of providing two or more metal and/or polymeric powders in a die, subjecting the two or more powders to high pressure to form a compact, sintering the compact to form a final porous metal or polymer of varying porosity, forming a stent from the porous metal or polymer and, optionally, loading at least one drug into the pores. The two or more powdered metals and/or polymers can comprise at least two different metals and/or polymers or can comprise one metal or polymer, the one metal or polymer provided in at least two different average particle sizes or can comprise several different metals or polymers provided in several different average particle sizes. In such a way, the porosity of the stent in different regions of the stent can be tailored by forming the stent of several different powdered metals or polymers comprising a combination of different elemental metals or alloys or polymers in powdered form, or using the same elemental metal, alloy or polymer but providing it in several powders of different average particle size or by some combination of different metals and/or polymers and same metals and/or polymers of different particle size.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An expandable intraluminal stent comprising a main body portion having a first end, a second end and a flow passage defined therethrough, the main body portion being sized for intraluminal placement within a body passage and subsequent expansion for implantation, at least a portion of the main body portion formed of at least one material having pores therein, the material having been formed from at least one powdered metal, the stent comprising at least two separate regions arranged along the length of the stent, the first region formed of a first material having first pores within, the first material characterized by a first porosity and a first mean pore size, the first material having been formed from a first powdered metal, the second region formed of a second material having second pores within, the second material characterized by a second porosity and a second mean pore size, the second material having been formed from a second powdered metal.

2. The stent of claim 1 wherein at least one of the first and second regions has a porosity of twenty to eighty percent by volume.

3. The stent of claim 2 wherein at least one of the first and second regions has a porosity of between forty and sixty percent of the total volume of the metal.

4. The stent of claim 1 formed of a plurality of strands of a metal, the metal having pores therein.

5. The stent of claim 1 wherein the stent is coated with one or more layers of one or more drug containing materials.

6. The stent of claim 1 wherein the first or second powdered metal is stainless steel.

7. The stent of claim 6 wherein the pores in the first and second materials contain at least one drug.

8. The stent of claim 7 wherein the drug is selected from the group consisting of smooth muscle cell inhibitors, collagen inhibitors, vasodilators, anti-platelet substances, anti-thrombotic substances, anti-coagulants, cholesterol reducing agents, angiogenics and combinations thereof.

9. The stent of claim 1 wherein the first pores contain a first drug and the second pores contain a second drug.

* * * * *